United States Patent [19]
Prammer

[11] Patent Number: 6,023,164
[45] Date of Patent: Feb. 8, 2000

[54] ECCENTRIC NMR WELL LOGGING APPARATUS AND METHOD

[75] Inventor: Manfred Prammer, Downingtown, Pa.

[73] Assignee: Numar Corporation, Malvern, Pa.

[21] Appl. No.: 09/027,824

[22] Filed: Feb. 20, 1998

[51] Int. Cl.[7] .................................................. G01V 3/00
[52] U.S. Cl. .......................................... 324/303; 324/318
[58] Field of Search ..................................... 324/303, 318, 324/322, 300, 307, 309

[56] References Cited

U.S. PATENT DOCUMENTS

| | | | |
|---|---|---|---|
| Re. 32,913 | 4/1989 | Clark ........................................ | 324/338 |
| 1,158,959 | 11/1915 | Beach . | |
| 2,912,641 | 11/1959 | Ruble . | |
| 2,973,471 | 2/1961 | Armistead et al. . | |
| 3,205,477 | 9/1965 | Kalbfell . | |
| 3,213,357 | 10/1965 | Brown et al. . | |
| 3,360,716 | 12/1967 | Bloom et al. . | |
| 3,395,337 | 7/1968 | Varian . | |
| 3,402,344 | 9/1968 | Brown et al. . | |
| 3,453,433 | 7/1969 | Alger et al. ............................ | 250/83.3 |
| 3,508,438 | 4/1970 | Alger et al. ............................ | 73/152 |
| 3,567,935 | 3/1971 | Nagel ..................................... | 250/83.1 |
| 3,567,936 | 3/1971 | Tittman .................................. | 250/83.1 |
| 3,590,228 | 6/1971 | Burke ..................................... | 235/151.35 |
| 3,593,116 | 7/1971 | Culpepper .............................. | 324/0.5 |
| 3,617,867 | 11/1971 | Herzog ................................... | 324/0.5 |
| 3,638,484 | 2/1972 | Tixier ..................................... | 73/152 |
| 3,657,730 | 4/1972 | Robinson et al. ...................... | 324/0.5 |
| 3,667,035 | 5/1972 | Slichter ................................. | 324/0.5 R |
| 3,777,560 | 12/1973 | Guignard ................................ | 73/151.5 |
| 3,784,898 | 1/1974 | Darley et al. ......................... | 324/0.5 R |
| 3,896,668 | 7/1975 | Anderson et al. ..................... | 73/152 |

(List continued on next page.)

FOREIGN PATENT DOCUMENTS

| | | | |
|---|---|---|---|
| 0 581 666 A3 | 2/1994 | European Pat. Off. .......... | G01V 3/32 |
| 0 649 035 B1 | 4/1995 | European Pat. Off. .......... | G01V 3/32 |

OTHER PUBLICATIONS

International Publication No. WO98/25164, Publication Date Jun. 11, 1998; from International Application No. PCT/US97/21889, Filed Nov. 26, 1997; Priority Data: Serial No. 08/759,829, Filed Dec. 04, 1996.

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Carr et al., "Effects of Diffusion on Free Precision in Nuclear Magnetic Resonance Experiments," *Physical Review*, vol. 94. No. 3 (May 1, 1954), pp. 630–638.

*Schlumberger Wireline & Testing*, "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

(List continued on next page.)

*Primary Examiner*—Louis Arana
*Attorney, Agent, or Firm*—Pennie & Edmonds LLP

[57] ABSTRACT

A method and apparatus are described using nuclear magnetic resonance (NMR) measurements for obtaining information relating to properties of geologic structures in highly conductive borehole environments. A centralized NMR logging probe is provided with a sleeve having a semi-circular RF shield that blocks signals from one side of the probe and with elements that press the uncovered side of the probe to the sidewall of the borehole. In highly conductive boreholes, the eccentrically-positioned modified probe results in increased signal-to-noise ratios and savings in peak power and energy compared with the use of standard centralized tools. The modified probe further suppresses unwanted NMR signals.

17 Claims, 2 Drawing Sheets

U.S. PATENT DOCUMENTS

| | | | |
|---|---|---|---|
| 4,291,271 | 9/1981 | Lauffer | 324/307 |
| 4,310,887 | 1/1982 | Suau | 364/422 |
| 4,528,508 | 7/1985 | Vail, III | 324/303 |
| 4,686,364 | 8/1987 | Herron | 250/256 |
| 4,710,713 | 12/1987 | Taicher et al. | 324/303 |
| 4,714,881 | 12/1987 | Givens | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,728,892 | 3/1988 | Vinegar et al. | 324/309 |
| 4,885,540 | 12/1989 | Snoddy et al. | 324/318 |
| 4,933,638 | 6/1990 | Kenyon et al. | 324/303 |
| 4,994,777 | 2/1991 | Leupold et al. | 335/302 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,122,746 | 6/1992 | King et al. | 324/307 |
| 5,212,447 | 5/1993 | Paltiel | 324/300 |
| 5,280,243 | 1/1994 | Miller | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,397,989 | 3/1995 | Spraul et al. | 324/321 |
| 5,412,320 | 5/1995 | Coates | 324/303 |
| 5,432,446 | 7/1995 | Macinnis et al. | 324/303 |
| 5,453,692 | 9/1995 | Takahashi et al. | 324/318 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,629,623 | 5/1997 | Sezginer et al. | 324/303 |
| 5,646,528 | 7/1997 | Hanley | 324/303 |
| 5,680,043 | 10/1997 | Hurlimann et al. | 324/303 |
| 5,705,927 | 1/1998 | Sezginer et al. | 324/303 |
| 5,796,252 | 8/1998 | Kleinberg et al. | 324/303 |

OTHER PUBLICATIONS

Kleinberg et al., "Novel NMR Apparatus for Investigating an External Sample," *Journal of Magnetic Resonance*, (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers* (1990), pp. 733–741.

Miller et al., "Spin Echo Magnetic Resonance Logging: Porosity and Free Fluid Index Determination," *Society of Petroleum Engineers* (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

Schlumberger Technology News—Oilfield Bulletin, "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs," SPWLA 35th Annual Logging Symposium (Jun. 26–29, 1995).

Prammer, M.G., "NMR Pore Size Distributions and Permeability at the Well Site," *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991), pp. 40–56.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Neuman et al., "Applications of Nuclear Magnetism Logging to Formation Evaluation," Journal of Petroleum Technology, vol. 34, (1982) pp. 2853–2862.

Chandler et al., Reliable Nuclear Magnetism Logging— With Examples in Effective Porosity and Residual.

Jackson et al., "Western Gas Sands Project Los Alamos NMR Well Logging Tool Development," Los Alamos National Laboratory (Oct. 1981—Sep. 1982) pp. 1–28.

Clavier et al., "The Theoretical and Experimental Bases for the 'Dual Water' Model for the Interpretation of Shaly Sands," *Journal of Petroleum Technology (Apr. 1984)*, pp. 3–15.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15(1979) No. 2, pp. 195–260.

Brownstein et al., "Importance of classical diffusion in NMR studies of water in biological cells," The American Physical Society, vol. 19, No. 6, (1979) pp. 2446–2453.

Farrar et al., "Pulse and Fourier Transform NMR Introduction to Theory and Methods," Academic Press (1971) pp. 26–29.

Waxman et al., "Electrical Conductivities in Oil–Bearing Shaly Sands," *Society of Petroleum Engineers Journal* (1968) pp. 107–122.

Brown et al., "Nuclear Magnetism Logging," Transactions of the American Institute of Mining, Metallurgical, and Petroleum Engineers, vol. 219 (1960), pp. 199–207.

ECCENTRIC NMR WELL LOGGING APPARATUS AND METHOD

FIELD OF THE INVENTION

The present invention relates to in situ nuclear magnetic resonance borehole measurements. More particularly, the invention is directed to a method and apparatus for measuring the petrophysical properties of a geologic formation in a highly conductive borehole environment.

BACKGROUND

As known in the art, nuclear magnetic resonance (NMR) logging methods provide a rapid non-destructive determination of porosity, movable fluid, permeability of rock formation and other parameters of interest. At least in part the wide-spread use of NMR logging is due to the fact that the measurements are environmentally safe and are unaffected by variations in the matrix mineralogy.

NMR logging is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the spin-spin relaxation time constant $T_2$ (also known as transverse relaxation time) which is an expression of the relaxation due to non-homogeneities in the local magnetic field over the sensing volume of the logging tool. In addition to $T_1$ and $T_2$, NMR logging tools are capable of measuring the fluid self-diffusion coefficient, a parameter which refers to the motion of atoms in a gaseous or liquid state due to their thermal energy. NMR measurements of the diffusion and the relaxation times provide information about the formation porosity, the composition and quantity of the formation fluid, and its viscosity, which are all parameters of considerable importance in borehole surveys.

NMR borehole measurements can be done using, for example, the centralized MRIL® tool made by NUMAR, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Millen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994). Details of the structure and the use of the MRIL® tool are also discussed in U.S. pat. Nos. 4,717,876; 4,717,877; 4,717,878; 5,212,447; 5,280,243; 5,309,098; 5,412,320; 5,517,115, 5,557,200 and 5,696,448, all of which are commonly owned by the assignee of the present invention. The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992. The content of the above patents and publications is hereby expressly incorporated by reference.

Both centralized and sidewall tools measure relaxation times and diffusion parameters of the formation within a certain volume, i.e., the "sensitive volume" of the tool, which is determined mainly by the shape of the magnetic field generated by the tool. Specifically, the boundaries of the sensitive volume of the tool are determined by the radiation patterns of the transmitting and receiving antennae as well as the structure of the magnetic field within the receiver's frequency passband.

Centralized tools, such as Numar's MRIL® tool, have an azimuthally uniform magnetic field with respect to the axis of the borehole. Thus, the sensitive volume of the tool is a cylindrical sheet residing in the formation surrounding the borehole. Changing certain measurement parameters of the tool, such as the operating frequency, causes the diameter of this cylinder to expand or contract. In general, such tools are designed to run centralized in the borehole. By contrast, sidewall tools measure NMR signals from only one direction, and therefore operate best when the sensitive part of the tool is close to the wall of the borehole.

Centralized NMR tools have a number of advantages but typically operate best in environments having moderate conductivity. However, their operation in a highly conductive environment, e.g., in salt saturated brine, is sometimes less than optimal. Highly conductive environments typically exist when the rock itself contains salt water. In such cases, to avoid an osmotic effect which may cause the rock to collapse, the borehole fluid must further be salt-saturated. The resulting high borehole conductivity reduces the signal-to-noise ratio of the NMR measurements, thus necessitating slow logging speeds. In addition, because of the strong signal attenuation, higher peak pulse power is required, which in turn results in the need for rapid discharges of the energy storing capacitors of the tool, and also results in shortened pulse echo trains.

Furthermore, the performance of a centralized tool in highly conductive environments is decreased because of an unwanted sodium resonance in the measured signal. Specifically, the tool's gradient field causes sodium nuclei (Na-23) to resonate at about one-half of the hydrogen diameter. The amplitude of the sodium signal is about 2.25 p.u. (porosity units) per 100 kppm NaCl concentration, with a decay time between about 5 and 35 msec. For a typical 16" diameter of investigation, the sodium resonance signal is at about 8", which can create problems for measurements in boreholes having diameters of about 7.5 to 8 inches.

A standard prior art method of dealing with these problems is to reduce the fluid volume around the probe using a fluid excluder, which makes the outer diameter of the tool larger. This approach addresses adequately problems associated with signal and pulse attenuation, however, it is not satisfactory because it reduces the probe's maneuverability and does not solve the sodium resonance problem.

Accordingly, there is a perceived need for a design of a centralized NMR probe that can be used in highly conductive boreholes.

SUMMARY OF THE INVENTION

The present invention provides an apparatus and method for using nuclear magnetic resonance (NMR) techniques for obtaining information relating to geologic structures surrounding highly conductive boreholes, e.g., in salt-saturated brine. In accordance with a preferred embodiment of the present invention, a centralized NMR tool is provided with an electro-magnetic shield covering one pole of the permanent magnet(s) of the tool, thus reducing the reception of signals from the direction of the covered magnet pole. The tool is further provided with elements that position the uncovered pole of the tool's magnet close to the sidewall of the borehole, i.e., eccentrically with respect to its axis. The apparatus and method in accordance with this invention can be used to suppress unwanted NMR signals during in-situ borehole logging measurements.

Specifically, there is provided in accordance with a preferred embodiment of the present invention, a centralized nuclear magnetic resonance (NMR) apparatus for conducting in-situ borehole measurements in a highly conductive environment comprising: a probe having at least one magnet with a north pole and a south pole, said at least one magnet generating a static magnetic field in the borehole, and having a longitudinal axis and magnetization direction substantially perpendicular to said longitudinal axis; a shield covering one of said north and south poles of said at least one magnet for reducing sensitivity of the probe to NMR signals from the corresponding magnetization direction; means for generating a time-variable magnetic field in a direction perpendicular to the static magnetic field; means for positioning the probe eccentrically within the borehole, such that the uncovered pole of said at least one magnet is positioned close to a sidewall of the borehole; and an antenna for receiving NMR signals from excited nuclei in the borehole.

Further, in accordance with a preferred embodiment of the invention, there is provided a method for conducting in-situ borehole logging measurements in highly conductive environments using a centralized NMR tool comprising the steps of: (a) providing a centralized tool having a probe with at least one magnet having a north pole and a south pole for generating a static magnetic field in the borehole, said at least one magnet having a longitudinal axis and magnetization direction substantially perpendicular to said longitudinal axis, wherein one of said north and south poles of said at least one magnet is covered with an electro-magnetic shield; (b) positioning the probe eccentrically within the borehole, such that the uncovered pole of said at least one magnet is close to a sidewall of the borehole; (c) generating a time variable magnetic field in a direction perpendicular to the static magnetic field; and (d) receiving NMR signals from excited nuclei in the material surrounding the borehole.

BRIEF DESCRIPTION OF THE DRAWINGS

The present invention will be understood and appreciated more fully from the following detailed description taken in conjunction with the drawings in which.

DETAILED DESCRIPTION

Figure 1:
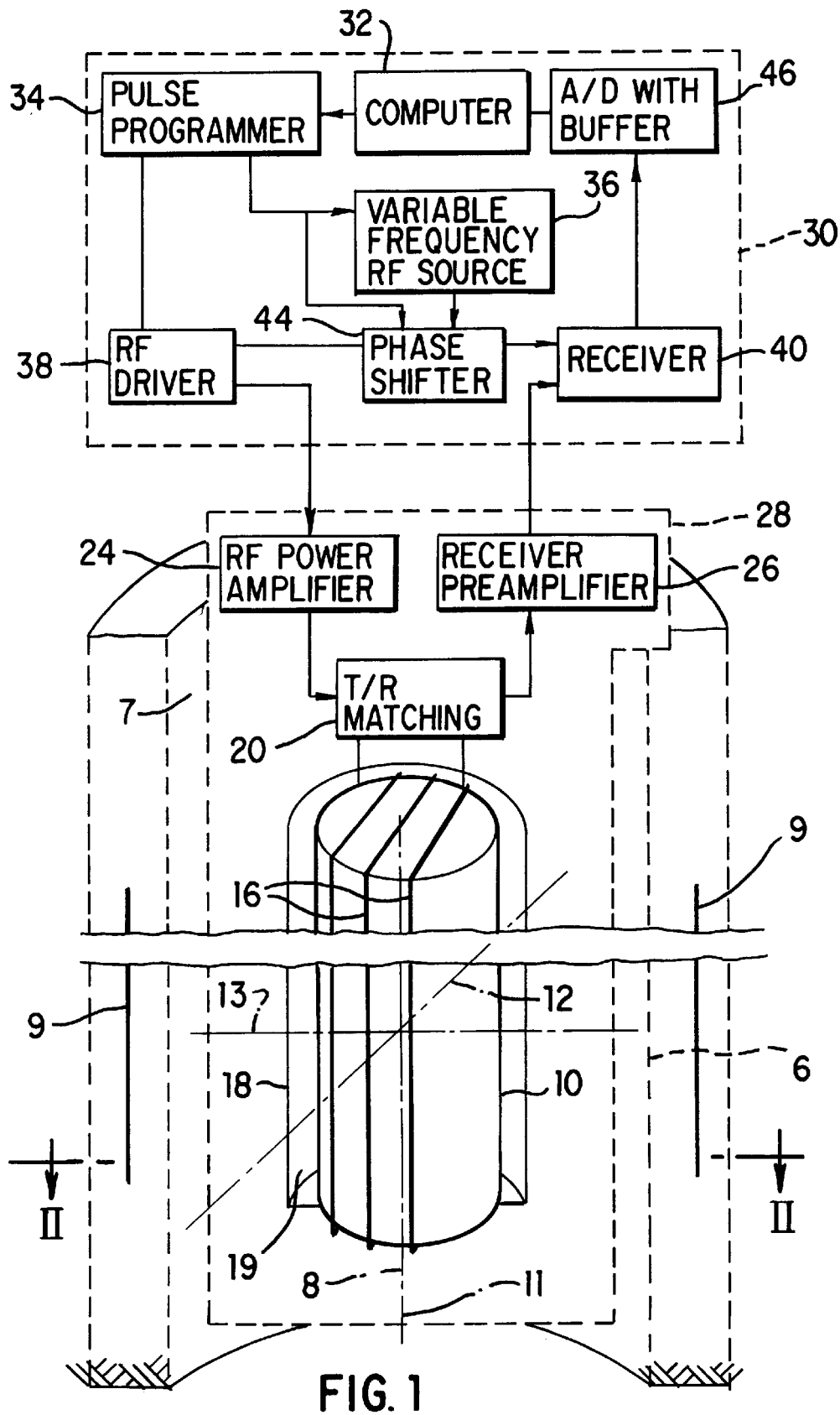
FIG. 1 is a partly pictorial and partly block diagram illustration of a MRIL® NMR well logging apparatus, which is modified in accordance with a preferred embodiment of the present invention for use in highly conductive environments.

Reference is now made to FIG. 1 which illustrates a prior art NMR logging apparatus which can be used in a modified form for NMR measurements in highly conductive environments in accordance with the present invention. In standard operation (no or mild conductivity), first portion 6 of the tool is arranged to be lowered into a borehole 7 having a borehole longitudinal axis 8 in order to examine properties of the geologic formation in the vicinity of borehole 7.

The first portion 6 comprises a generally cylindrical permanent magnet 10, preferably having a longitudinal axis 11 which is preferably coaxial with the longitudinal axis 8 of the borehole. Alternatively, a plurality of permanent magnets 10 may be employed. Hereinafter, the one or more permanent magnets 10 will be considered together and referred to as permanent magnet 10 and their common longitudinal axis will be identified as longitudinal axis 11. Permanent magnet 10 preferably has uniform magnetization substantially perpendicular to the longitudinal axis of the logging tool, which is parallel to the longitudinal axis 8 of the borehole 7. The permanent magnet is typically formed of a ferrite permanent material.

The first portion 6 also comprises one or more coil windings 16 which preferably are arranged on top of the permanent magnet and form the tool antenna. The magnetization direction 13 created by the antenna is substantially perpendicular to the longitudinal axis 11 of the bore hole.

The coil windings 16, together with a transmitter/receiver (T/R) matching circuit 20 define a transmitter/receiver (T/R) circuit. T/R matching circuit 20 typically includes a resonance capacitor, a T/R switch and both to-transmitter and to-receiver matching circuitry and is coupled to a first RF power amplifier 24 and to a receiver preamplifier 26.

The permanent magnet 10 and coil windings 16 are preferably housed in a non-conductive, non-ferromagnetic protective housing 18. The housing and its contents will hereinafter be referred to as the probe 19.

In operation, the probe along with RF amplifier 24, preamplifier 26 and T/R matching circuit 20, designated collectively as housing 28 are passed through the borehole. Alternatively, some of the above elements may be located above ground in housing 30.

Disposed in a housing indicated in FIG. 1 by block 30, is a control circuitry, including a computer 32, which provides a control output to a pulse programmer 34. Pulse programmer 34 controls the operation of phase shifter 44, as well as an RF driver 38, which drives RF power amplifier 24. Pulse programmer 34 controls the operation of a variable frequency RF source 36, the output of which is passed through phase shifter 44 to the RF driver 38. The signal from RF driver 38 is amplified in RF power amplifier 24 and passed through T/R matching circuit 20 to the antenna 16. The NMR pulse sequences used in a preferred embodiment are known in the art and will not be considered in further detail.

NMR signals from excited nuclei in the formation surrounding the borehole are picked up by the receiving antenna 16 and passed through T/R matching circuit 20 to RF receiver preamplifier 26, the output of which is supplied to an RF receiver 40 which also receives an input from phase shifter 44. Receiver 40 outputs via an A/D converter with a buffer 46 to the computer 32 for providing desired well logging output data for further use and analysis.

Further details of the construction and operation of tools in accordance with the present invention can be found in U.S. Pat. Nos. 4,710,713 4,717,876; 4,717,877; 4,717,878; 5,212,447; 5,280,243; 5,309,098; 5,412,320; 5,517,115, 5,557,200 and 5,696,448 all of which are commonly owned by the assignee of the present invention. The content of the above patents and publications is hereby expressly incorporated by reference.

Figure 2:
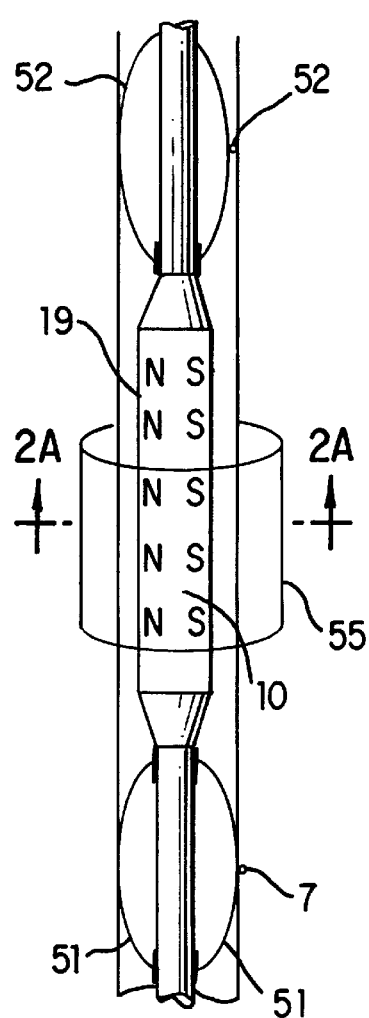
FIG. 2 is an illustration of a well logging apparatus, such as shown in FIG. 1, being positioned centrally within a borehole for obtaining NMR measurements of a geologic formation surrounding a borehole.

FIG. 2 is an illustration of a well logging apparatus, such as shown in FIG. 1, being positioned centrally within a borehole for obtaining NMR measurements of a geologic formation surrounding a borehole. As shown, placement of the probe 19 coaxial with the axis of the borehole is achieved with the use of an upper centralizer 52 and lower centralizer 51 placed symmetrically above and below the probe 19. In a specific embodiment shown in FIG. 2, the upper and lower centralizers are implemented using two or more bow springs positioned in a diametrically opposite manner, so that when the probe is lowered in the borehole, they lean on the walls of the borehole and centralize the probe with respect to the borehole's axis. FIG. 2 also illustrates a cylindrical sensitive volume 55 in the formation surrounding the borehole when a NMR tool, such as the MRIL® tool shown in FIG. 1 is used.

Figure 2A:
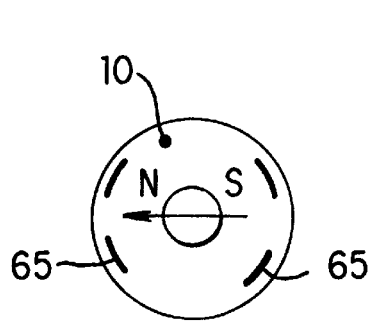
FIG. 2A is a cross-sectional view of section A—A of the apparatus of FIG. 2.

FIG. 2A shows a cross-sectional view of the magnet 10 with N-pole and S-pole sides of the magnet depicted, along with their magnetization direction and the legs 65 of the antenna.

Figure 3:
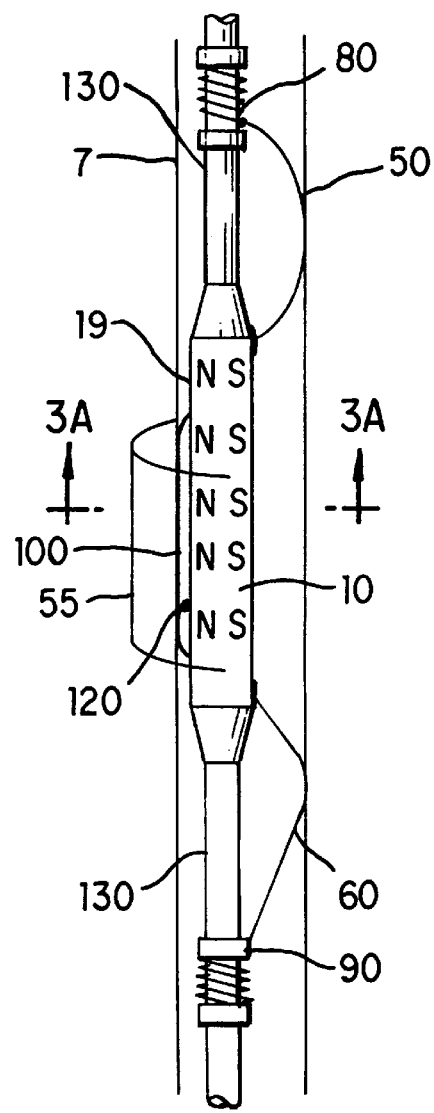
FIG. 3 is an illustration of a well logging apparatus as modified and used in accordance with a preferred embodiment of the present invention for obtaining NMR measurements in highly conductive boreholes.

FIG. 3 illustrates an NMR probe 19 configured and positioned in a borehole in accordance with a preferred embodiment of the present invention for use in highly conductive borehole environments. In a preferred embodiment, a standard NMR tool, such as the centralized MRIL® of Numar Corporation can be used as a basis suitable for modification in accordance with the principles of the present invention.

In particular, to reduce and possibly eliminate disadvantages associated with operating a centralized NMR tool in a highly conductive environment, in accordance with a preferred embodiment of the present invention, a cylindrical sleeve 100, preferably made of fiberglass, is installed over the probe housing. The sleeve 100 includes, or has embedded therein, a semi-circular RF shield 110 that is positioned as to cover one of the poles of the permanent magnet of the probe and the corresponding portion of the RF antenna. The shield 110 is preferably made of copper and can be very thin, i.e., less than a millimeter. In a preferred embodiment, the shield is positioned very close to, but makes no contact with the legs 65 of the tool antenna. In general, the length of the shield corresponds to the length of the tool antenna, which for the MRIL® tool is 24".

The shield 110 used in accordance with the present invention effectively reduces sensitivity to NMR signals emitted from the covered-pole side of the probe. It has been determined that this configuration attenuates NMR signals from the covered hemisphere (which in the embodiment shown in FIG. 3 is the south pole) by about 50%. Accordingly, the sensitivity of the tool to signals from its uncovered side is higher compared with that of the covered side, so the tool is no longer truly "centralized" in terms of its sensitivity.

In alternative embodiments of the present invention, sleeve 100 can be made, at least in part, of materials which provide extra strength and durability. For example, in a specific embodiment a half-cylinder portion of sleeve 100 that falls behind the covered pole of the magnet can be made of steel. It should be apparent that in this embodiment the sleeve may serve itself as an RF shield. Alternatively, a copper shield 110, as described above, can also be enclosed in the sleeve because of its superior electromagnetic properties.

To further increase the sensitivity of the probe to signals from its uncovered side, in accordance with a preferred embodiment of the present invention, one or more eccentralizers are used to press the uncovered side of the probe closer to the sidewall of the borehole. Eccentralizers are known in the art, where they are used primarily with sidewall tools, which by design have to be placed eccentrically with respect to the borehole. A number of them are powered devices, comprising a hydraulically or electrically actuated pistons having a pad at one end. The pistons extend from the tool on command and press the pad at their ends to a sidewall of the borehole, thus moving the tool away from that wall. In accordance with a specific embodiment of the present invention (not shown in the drawings), one or more powered eccentralizers of the type discussed above are used to further increase the sensitivity of the probe. Since these devices are known in the art, there is no need to describe them in further detail.

Figure 3A:
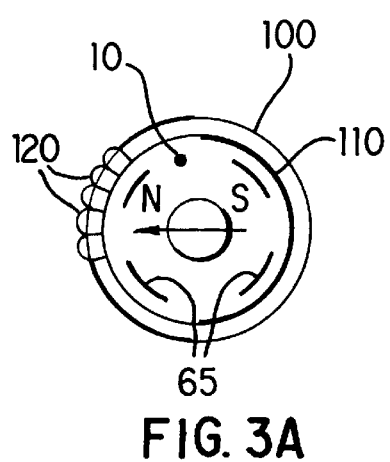
FIG. 3A is a cross-sectional view of section B-B of the apparatus of FIG. 3.

In a preferred embodiment of the present invention, passive eccentralizers can be used to perform the function of pressing the uncovered side of the probe to the sidewall of the borehole. Using a passive instead of a powered device has the advantage of having simpler design which is convenient and less costly to manufacture and operate. With reference to FIGS. 3 and 3A, such a passive design is implemented in a specific embodiment using one or more bow springs 50 and 60.

As shown in FIG. 3, in a preferred embodiment two bow springs are attached above and below the probe 19 along its axis, directly behind the covered pole of the magnet. One end of each bow spring 50 and 60 is attached to a coil spring 80 and 90, respectively, positioned on the neck 130 of the tool that carries the probe. In a preferred embodiment, the second ends of the bow springs 50, 60 are attached to the fiberglass sleeve 100. Using this arrangement, the bow springs 50, 60 are always under compression. In a preferred embodiment, this attachment can be made by fixing the end of the bow to a steel insert secured to the sleeve 100 at holes drilled in it.

In alternative embodiments of the present invention, which are not shown in the drawings, one or more bow springs attached at both ends to the probe itself can be used alone or in combination with separate bow springs positioned above/below the probe to press the probe to the sidewall of the borehole. For example, with reference to FIG. 3, such probe-attached bow spring can be used along with bow spring 50, 60 or both to this end.

In operation, the arc of bow springs 50, 60 leans on the sidewall of the borehole and presses the uncovered side of the probe to the diametrically opposite sidewall of the borehole. To this end, in a preferred embodiment the bow springs are made of highly tensile material, such as stainless steel or beryllium copper.

In a preferred embodiment, the arc of the springs 50, 60 can be varied within certain limits by changing the position of the coil springs 80, 90 along the neck portion 130, as to adjust to boreholes with different diameters.

To avoid differential sticking, in a preferred embodiment of the present invention the probe is further provided with rubber fins 120, attached to the sleeve 100. In a preferred embodiment, the rubber fins 120 are about 0.5 inch wide, 0.5 inch thick and 24 inches long (corresponding to the length of the MRIL® antenna). Rubber fins 120 provide clearance, preferably about 0.5", between the probe 19 and the sidewall 7 of the borehole as to avoid sticking. In a preferred embodiment, fins 120 can be detachably mounted to the sleeve 100 as to permit their replacement when they wear off. Alternatively, the fins 120 may be glued to the sleeve 100.

FIG. 3A is a cross-sectional view of the probe 19 illustrating the magnet 10 with its N-pole and S-pole sides, the legs 65 of the antenna and the rubber fins 120.

It should be noted that in deviated (i.e., non-vertical) boreholes, the probe 19 will fall on the lower side of the hole under its own weight. However, due to the bow springs 50, 60 of the tool modified in accordance with the present invention, the probe will orient itself in such manner that the uncovered, sensitive side of the probe will be close to the borehole's lower sidewall. This is another advantage of the probe built and operated in accordance with the present invention.

In operation, the eccentric probe of the present invention is positioned eccentrically within the borehole such that one pole of the permanent magnet, which is not covered by the shield (i.e., the N-pole side) is closer to the sidewall of the borehole than the covered-pole side of the probe. Consequently, there is substantially less borehole fluid in the space between the uncovered, sensitive side of the eccentric probe and the borehole wall compared with the case of a standard centralized tool. Thus, in highly conductive environment the eccentric NMR probe in accordance with the present invention will exhibit less signal and pulse attenuation compared to standard centralized probes.

In a preferred embodiment of the method of the present invention, measurements in borehole environments that exhibit no or only mild conductivity are performed using a centralized NMR tool, such as Numar's MRIL® tool, concentrically placed in the borehole. In cases when the borehole is determined to be highly conductive, the tool can be equipped with a fiberglass sleeve 100 which has a semicircular RF shield to reduce the signals from one direction, as well as elements that would press the uncovered, sensitive side of the probe to the sidewall of the borehole. In a preferred embodiment of the present invention, these elements comprise the bow springs and rubber fins described above. Modification of these elements, as known in the art, can be used in alternative embodiments. Accordingly, the present invention provides a simple modular approach to extending the use of existing centralized NMR tools to highly conductive measurement environments.

Experimental Results

Preliminary experiments with the eccentric NMR probe built and operated in accordance with the present invention indicate that in a non-conductive environment the reduction of the sensitive volume of the probe reduces the received NMR signals by about 40% compared with measurements using the standard centralized tool. However, in highly conductive fluid environment, this loss in signal strength is compensated by an increase in the Q-factor of the probe of about 2.5, resulting in a signal-to-noise ratio (SNR) approximately the same as for the centralized tool in non-conductive environment.

In particular, the Q-factor of the eccentric probe is about 2.5 times that of the standard concentric system at the design limit of 0.02 ohm-m in a 8.5" borehole. This increase in the Q-factor provides savings of 2.5 in terms of energy and peak pulse power required. Given the same available energy, pulse trains can be extended by a factor of 2.5.

As to the unwanted sodium resonance signals encountered in highly conductive environments, it is expected that for the tool made and operated in accordance with the present invention, such signals will decrease from a typical value of about 5.5 porosity units (p.u.), as in the case of a concentrically placed probe in 250 kppm NaCl brine, to a much more acceptable (porosity dependent) value of about 1 p.u.

Although the present invention has been described in connection with the preferred embodiment, it is not intended to be limited to the specific form set forth herein, but is intended to cover such modifications, alternatives, and equivalents as can be reasonably included within the spirit and scope of the invention as defined by the appended claims.

What is claimed is:

1. A centralized nuclear magnetic resonance (NMR) apparatus for conducting in-situ borehole measurements in a highly conductive environment comprising:

a probe having a longitudinal axis and at least one magnet with a north pole and a south pole, said at least one magnet generating a static magnetic field in the borehole with magnetization direction substantially perpendicular to said longitudinal axis;

a shield covering one of said north and south poles of said at least one magnet for reducing sensitivity of the probe to NMR signals from the corresponding magnetization direction;

means for generating a time-variable magnetic field in a direction perpendicular to the static magnetic field;

means for positioning the probe eccentrically within the borehole, such that the uncovered pole of said at least one magnet is positioned close to a sidewall of the borehole; and an antenna for receiving NMR signals from excited nuclei in the borehole.

2. The apparatus of claim 1 wherein the shield is half-cylindrical.

3. The apparatus of claim 2 wherein the shield is enclosed in a sleeve surrounding the probe.

4. The apparatus of claim 3 further comprising rubber fins attached to the sleeve on the uncovered side of the probe.

5. The apparatus of claim 4 wherein the rubber fins are approximately 0.5" wide and run along the longitudinal axis of the probe.

6. The apparatus of claim 2 wherein the sleeve is made of non-conductive material.

7. The apparatus of claim 2 wherein the shield is enclosed in a half-cylindrical sleeve.

8. The apparatus of claim 7 wherein the half-cylindrical sleeve is made of a conductive material and also serves as a shield.

9. The apparatus of claim 1 wherein the shield is made of copper.

10. The apparatus of claim 1 wherein the means for positioning the probe eccentrically comprises:

one or more bow springs attached to the probe directly behind the covered pole of said at least one magnet, said one or more bow springs pressing the uncovered side of the probe to the diametrically opposite sidewall of the borehole.

11. The apparatus of claim 1 further comprising a sleeve surrounding the probe, the means for positioning the probe eccentrically comprises:

one or more bow springs attached to the probe directly behind the covered pole of said at least one magnet, said one or more bow springs pressing the uncovered side of the probe to the diametrically opposite sidewall of the borehole, wherein at least one end of said one or more bow springs is fixed to the sleeve.

12. The apparatus of claim 11 further comprising rubber fins attached to the sleeve on the uncovered side of the probe.

13. The apparatus of claim 1 wherein the means for positioning the probe eccentrically comprises one or more powered eccentralizers.

14. The apparatus of claim 1 wherein the generated static magnetic field is a gradient field.

15. A method for conducting in-situ borehole logging measurements in highly conductive environments using a centralized NMR tool comprising the steps of:

(a) providing a centralized tool having a probe with a longitudinal axis and at least one magnet having a north pole and a south pole for generating a static magnetic field in a borehole with magnetization direction substantially perpendicular to said longitudinal axis, wherein one of said north and south poles of said at least one magnet is covered with an electromagnetic shield;

(b) positioning the probe eccentrically within the borehole, such that the uncovered pole of said at least one magnet is close to a sidewall of the borehole;

(c) generating a time variable magnetic field in a direction perpendicular to the static magnetic field; and (d) receiving NMR signals from excited nuclei in the material surrounding the borehole.

16. A method for suppressing unwanted NMR signals during in-situ borehole logging measurements in highly conductive environments using a centralized NMR tool, comprising the steps of:

(a) in a borehole having radius R, providing a centralized tool with a longitudinal axis and sensitive volume extending approximately 2R from said axis, the tool having a probe with at least one magnet having a north pole and a south pole for generating a static gradient magnetic field substantially azimuthally uniform about the longitudinal axis, wherein one of said north and south poles of said at least one magnet is covered with an electro-magnetic shield;

(b) positioning the probe eccentrically within the borehole, such that the uncovered pole of said at least one magnet is close to a sidewall of the borehole;

(c) generating a time variable magnetic field in a direction perpendicular to the static magnetic field; and (d) receiving NMR signals from excited nuclei in the material surrounding the borehole, wherein unwanted NMR signals originating near the sidewall of the borehole are suppressed.

17. The method of claim 16 wherein the unwanted NMR signals are due to a sodium resonance in the highly conductive environment.

* * * * *